(12) United States Patent
Cabatic et al.

(10) Patent No.: US 6,604,630 B1
(45) Date of Patent: Aug. 12, 2003

(54) CARRYING CASE FOR LIGHTWEIGHT ULTRASOUND DEVICE

(75) Inventors: Bryan S. Cabatic, Seattle, WA (US); Stephanie Barnes, Bothell, WA (US); Steven Bunce, Sedro Woolley, WA (US); Patrick Martin, Seattle, WA (US); Bricin Epps, Seattle, WA (US); Carol Perron, Redmond, WA (US)

(73) Assignee: Sonosite, Inc., Bothell, WA (US)

( * ) Notice: Subject to any disclaimer, the term of this patent is extended or adjusted under 35 U.S.C. 154(b) by 0 days.

(21) Appl. No.: 10/066,337

(22) Filed: Jan. 30, 2002

(51) Int. Cl.⁷ ............................. B65D 85/38
(52) U.S. Cl. ............. 206/305; 206/569; 206/570; 383/39; 383/113; 383/119
(58) Field of Search ............... 206/305, 320, 206/569, 570, 572; 361/679; 383/6, 7, 38, 39, 40, 109, 113, 119, 121.1

(56) References Cited

U.S. PATENT DOCUMENTS

| | | | |
|---|---|---|---|
| 4,020,930 A | | 5/1977 | Weber |
| 4,429,793 A | * | 2/1984 | Ehmann ............... 206/570 |
| 4,738,547 A | * | 4/1988 | Brown ................. 383/119 |
| 4,852,783 A | * | 8/1989 | Bryden et al. ......... 383/39 |
| 4,967,986 A | * | 11/1990 | Schildkraut ........... 383/39 |
| 5,207,303 A | | 5/1993 | Oswalt et al. |
| 5,260,884 A | | 11/1993 | Stern |
| 5,437,367 A | | 8/1995 | Martin |
| 5,607,054 A | | 3/1997 | Hollingsworth |
| 5,743,649 A | * | 4/1998 | Gonzalez .............. 383/39 |
| 5,848,700 A | | 12/1998 | Horn |
| 6,173,835 B1 | | 1/2001 | Swinger et al. |
| 6,220,436 B1 | * | 4/2001 | Chung ................. 383/119 |
| 6,291,171 B1 | * | 9/2001 | Ricciardi et al. ...... 206/570 |

* cited by examiner

Primary Examiner—Luan K. Bui
(74) Attorney, Agent, or Firm—Townsend and Townsend and Crew LLP

(57) ABSTRACT

A carrying case is dimensioned to present a lightweight ultrasound device and one or more accessory products in an organized fashion, to a physician to reduce set up time for diagnostic examinations. The carrying case having a handle and at least one fastener for securing the carrying case in a closed configuration. The carry case comprising at least one instrument panel, the instrument panel having a top side edge and a bottom edge, and having a plurality of harnesses for the secure positioning of a lightweight ultrasound device, a data recording device and at least one transducer, the instrument panel being substantially inflexible, a first accessory panel being flexibly connected to the top edge of the instrument panel such that the first accessory panel may be folded over the instrument panel.

46 Claims, 4 Drawing Sheets

CARRYING CASE FOR LIGHTWEIGHT ULTRASOUND DEVICE

BACKGROUND OF THE INVENTION

1. Field of the Invention

The present invention relates to a carrying case designed for use with a lightweight ultrasound device. The carrying case is designed to provide a sonographer or physician with a carrying case that allows quick set up and take down of the ultrasonic device before and after an ultrasonic examination.

2. Description of the Prior Art

A variety of carrying cases are presently used for medical purposes. Most common among them are carry cases for emergency medical kits where portability of emergency medical supplies, such as bandages, drugs and wound treatment materials, is important in order for a doctor, or emergency medical technician, to reach an injured person for the purpose of administering emergency treatment. Along with carrying cases for medical kits and supplies, a limited number of carrying cases exist for transporting diagnostic equipment from a hospital or ambulance to a patient in the field. In non-emergency situations, medical equipment can be transported using hand carts or hand trucks. For the most part though, medical diagnostic equipment is not considered portable and so there has not been a need for a carrying case for such diagnostic equipment.

There is a need for a carrying case for a lightweight ultrasound system such that a user (physician, sonographer, EMT or the like) can transport the diagnostic equipment to a patient quickly, easily and efficiently. There further is a need for a carrying case that is ergonomically designed to permit a quick ultrasound diagnosis while recording the exam for medical records or future analysis. It is further desirable if a carrying case for a lightweight ultrasound device would permit a user to use the device without removing the ultrasound device from the case, and allow the user to arrange the case in a variety of configurations depending on the available space both vertically and horizontally. It would be further advantageous if a carrying case provided a user with all the accessory products he or she might need to perform a variety of ultrasound diagnostic exams such that the right exam is administered to a patient for the appropriate need.

BRIEF SUMMARY OF THE INVENTION

It is therefore, an objective of the present invention to provide a carrying case for a lightweight ultrasound device that will permit a user to set up, scan, and record quickly, and allow equally quick take down.

Furthermore, it is an object of the present invention to permit the set-up of the lightweight ultrasound device in a variety of settings, including areas where horizontal space is at a premium.

It is still a further objective to have a carrying case for a lightweight diagnostic ultrasound device that will carry a variety of accessory products, and a data recorder so the ultrasound scan can be adapted to the needs of the patient, and the scan can be saved for later review or uplink.

The present invention relates generally to a carrying case for use with a lightweight ultrasound system. The carrying case is dimensioned to encase a lightweight ultrasound device and one or more accessory products, in an organized fashion to a user to reduce set up time for diagnostic examinations. The carrying case has a handle and at least one fastener for securing the carrying case in a closed configuration. The carrying case comprises at least one instrument panel, the instrument panel having a top side edge and a bottom edge, and includes a plurality of harnesses for the secure positioning of a lightweight ultrasound device, a data recording device and at least one transducer. The instrument panel is substantially inflexible, and a first accessory panel is flexibly connected to the top edge of the instrument panel such that the first accessory panel may be folded over the instrument panel such that the first accessory panel and the instrument panel lay substantially parallel to each other. The first accessory panel has one or more pockets for the secure retention of accessory products needed to perform a diagnostic ultrasound scan, and a second accessory panel is optionally flexibly connected to the bottom edge of the instrument panel such that the second accessory panel may be folded over the instrument panel, and lay substantially parallel to both other panels. The second accessory panel preferably includes a substantially form fitted pocket for retention of a container of acoustic gel and one or more pockets for the secure retention of accessory products needed to perform a diagnostic ultrasound scan. In this way, the carrying case arranges the lightweight ultrasound device, the data recording device and all accessories at the ready when opened. The system components are securely positioned when the case is closed, and the carrying case may be opened and closed easily and quickly to switch between access and storage functioning.

Alternatively, the invention comprises a carrying case for holding a lightweight ultrasound device which is formed in a tri-fold arrangement such that the carrying case may be easily transported when closed and permit easy access to the hand held ultrasound device when open. The tri-fold arrangement comprises a top panel having an interior face with a flat panel display, a means for securing the flat panel display in place, an exterior face, a first fastening element, a top margin connected to the top panel and having a support spine for the attachment of at least one weight bearing handle, a reinforced center panel connected to the top margin opposite the top panel and having a harness for firmly holding a lightweight ultrasound device, a means for attaching a data storage device, a means for attaching a power supply for the flat panel display, a padded bottom margin connected to the center panel, and a bottom panel being connected to the bottom margin opposite the center panel. The bottom panel has an interior surface having one or more pockets and an exterior surface having a second fastening element. When the top panel and bottom panel are folded over the center panel, the top margin and bottom margin form perpendicular support structures, and the first fastening element and the second fastening element may be connected to secure the top panel and the bottom panel in a closed position.

In another embodiment, the present invention comprises a carrying case for a lightweight ultrasound device comprising a flexible tri-leaf body formed from an outer shell and an inner lining sewn together, wherein a margin separates each leaf, the body forming a carrying case when properly folded, and lies substantially flat when open. The tri-leaf body comprises a first leaf having at least one pocket, and a second leaf having a substantially rigid insert between the outer shell and the inner lining. The second leaf has a harness for securely retaining a lightweight ultrasound device, and a mounting area for one or more peripheral device(s). A third leaf has at least one pocket and a first margin separating the first leaf and the second leaf, wherein a weight bearing spine is constructed between the shell and the lining so that a handle may be attached to the spine and support the weight of the carrying case when closed. A second margin separating the second leaf and the third leaf is also preferably provided, wherein a protective padding is inserted between the shell and the lining, and a reusable fastening means for securing the carrying case in the closed position.

Other objects and advantages of the present invention will become apparent from the following description of the drawings taken in conjunction with the accompanying drawings wherein like parts in each of the several figures are identified by the same reference numerals.

DETAILED DESCRIPTION OF THE INVENTION

For purposes of clarification a number of terms are used with specific meaning in the description of the present invention which are either designed to be interchangeable for discussion purposes in order to better present the invention in text, or to clarify the particular meaning the inventors prefer when using a particular word. The language selected for clarification is as follows:

The term Panel and Leaf are used somewhat interchangeably. The use of the word panel refers to a stiffer structure than the word leaf as used herein, and in the claims description, the words are considered interchangeable when discussing the dependent claim elements where additional properties are added to either a leaf or a panel.

A Lightweight Ultrasound Device refers to a portable or hand held ultrasound system dimensioned both in size and weight to be small enough to fit within the present invention. For ease of reference, the inventors disclaim any ultrasound system having a weight in excess of 5 kg, or having a long axis dimension in excess of 50 cm. In general, the lightweight ultrasound device used with the present invention are ordinarily in the class of hand held diagnostic ultrasound devices.

The present invention can be generally characterized as a carrying case for a lightweight ultrasound device, configured in a manner to allow portability of the device and its accessories, and allowing for quick set up and take down to increase user efficiency. The use of a data recording device permits the recording of the ultrasound examination. The carrying case in the preferred embodiment has a tri-leaf or three panel design. The orientation is for a central main panel to which the lightweight ultrasound device is secured to. The central panel or center leaf has a reinforced backing to better carry the weight of the ultrasound device, a data storage device and one or more peripheral devices. Oriented on the top and bottom of the center panel are accessory panels having varying functional elements incorporated into them. Primarily the top and bottom are designed to provide storage space for necessary components a physician may need to perform a diagnostic ultrasound scan, or provide for a viewing means so a patient, or audience can see the ultrasound scan. The carrying case is envisioned as both a "soft" and "hard" luggage construction depending on the environment the user intends to take the lightweight ultrasound system to. For a more complete description, please refer to the accompanying drawings.

Figure 1A:
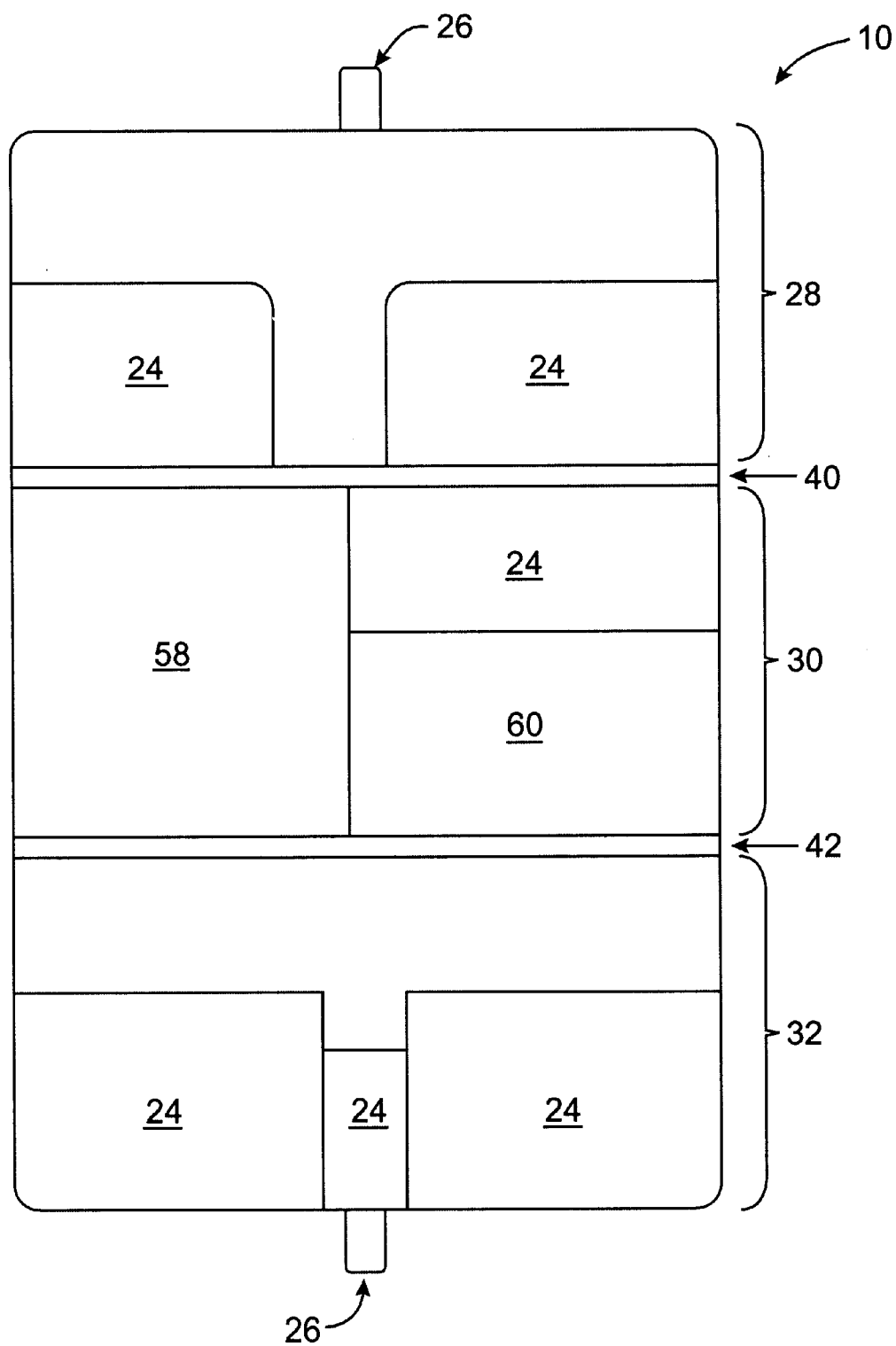
FIG. 1A illustrates the basic form of the carrying case
Figure 1B:
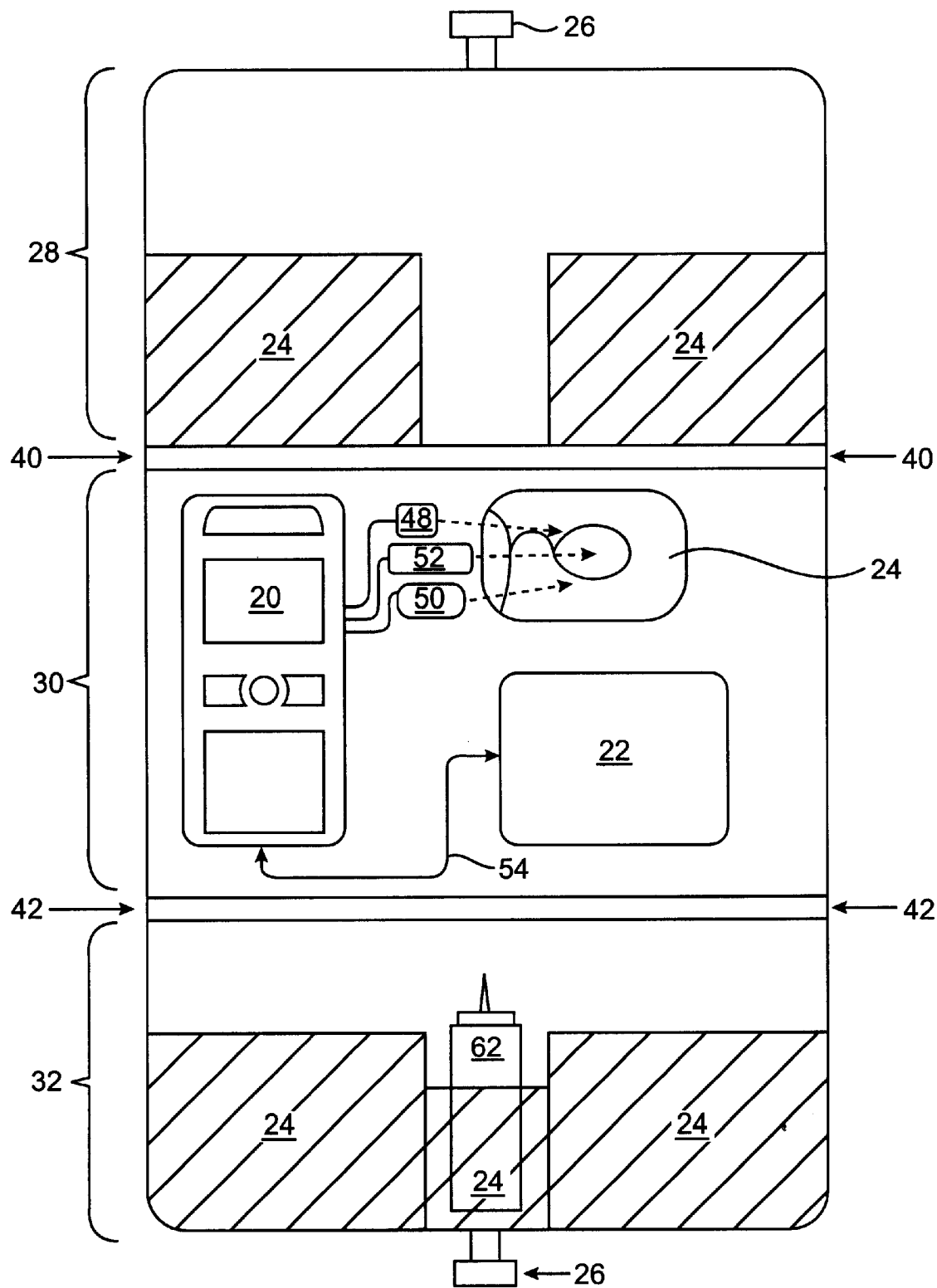
FIG. 1B shows the loaded carrying case.
Figure 2:
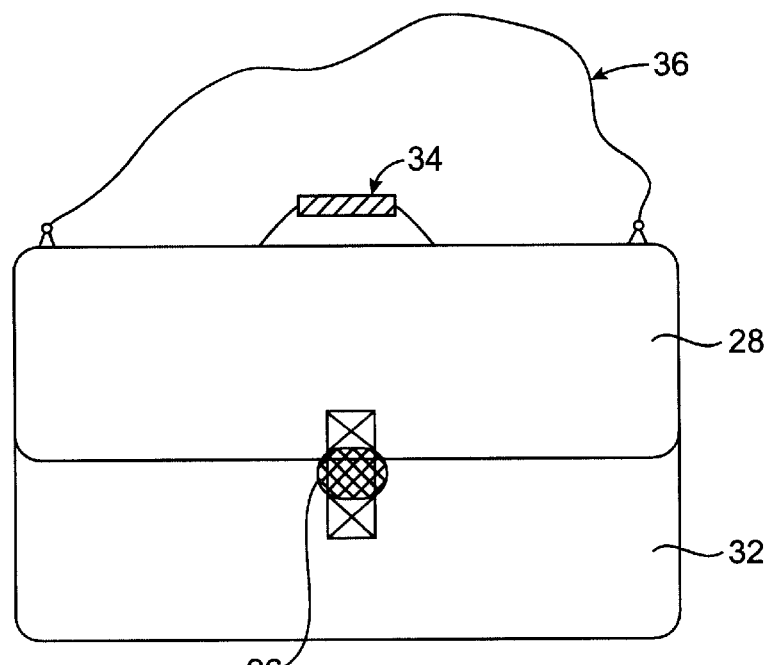
FIG. 2 shows a plan view of the closed carrying case.
Figure 3:
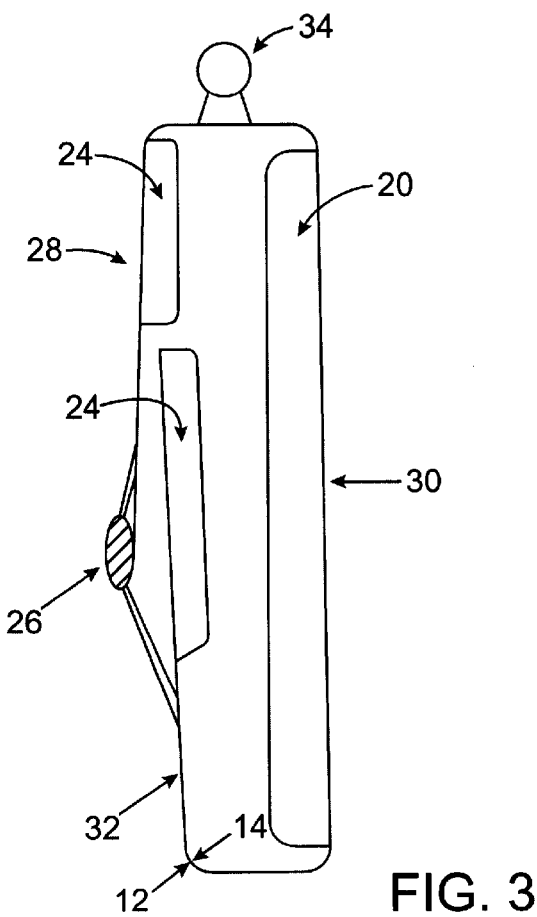
FIG. 3 shows a side view of the closed carrying case.
Figure 4:
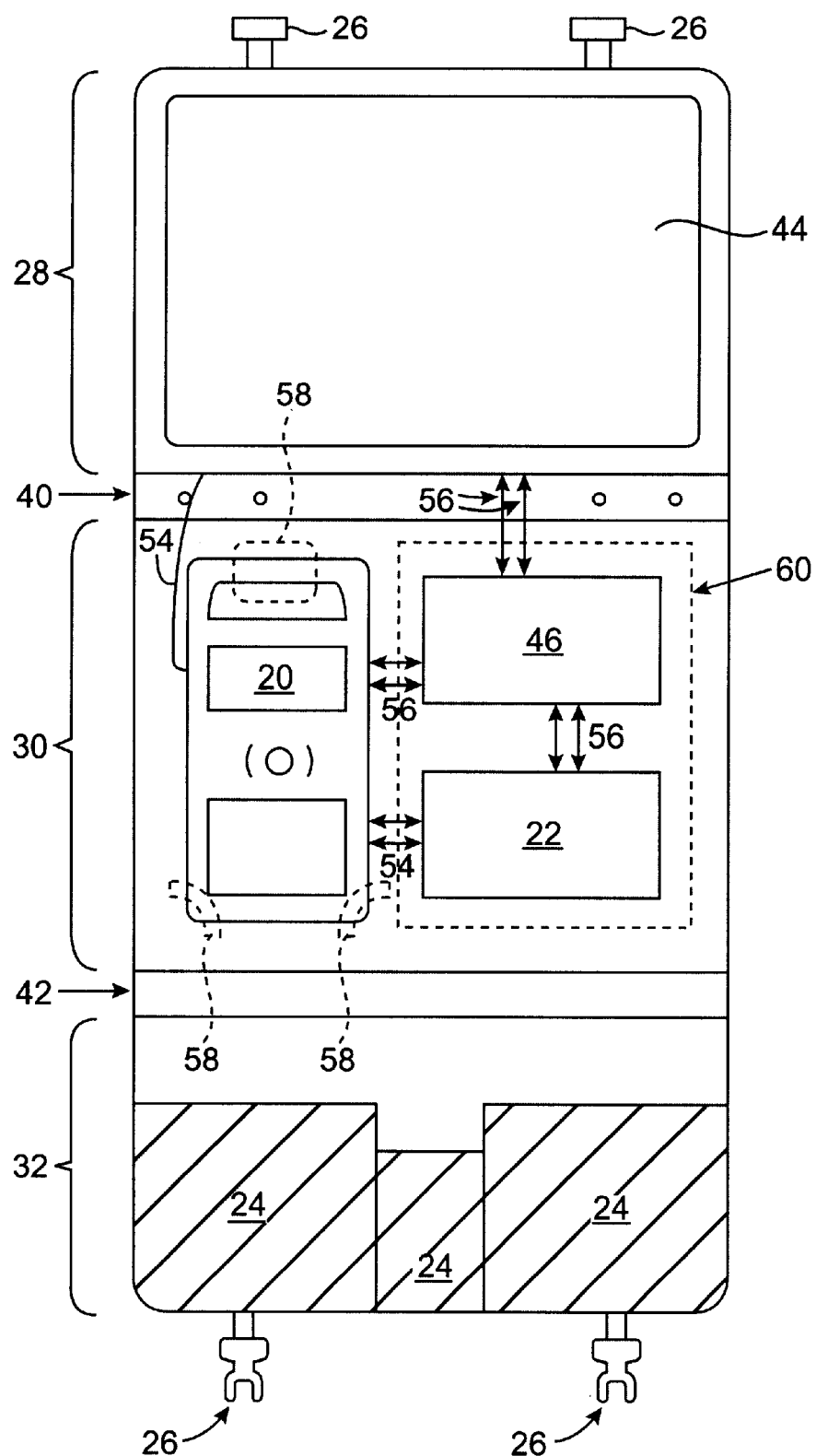
FIG. 4 shows a carrying case incorporating a flat panel display in the carrying case.

Referring now to FIGS. 1–4, the carrying case 10 is dimensioned to present a lightweight ultrasound device 20 and one or more accessory products 22 in an organized fashion, to a physician or sonographer to reduce set up time for diagnostic examinations. The carrying case 10 has a handle 34 and at least one fastener 26 for securing the carrying case 10 in a closed configuration. The carry case 10 comprising at least one instrument panel 30 having a top edge and a bottom edge, and having a plurality of harnesses 58 for the secure positioning of a lightweight ultrasound device 20, a data recording device 22 and at least one transducer 48, the instrument panel 30 being substantially inflexible. A first accessory panel 28 is flexibly connected to the top edge of the instrument panel 30 such that the first accessory panel 28 may be folded over the instrument panel 30 such that the first accessory panel 28 and the instrument panel 30 lay substantially parallel (see FIG. 3), the first accessory panel 28 having one or more pockets 24 for the secure retention of accessory products needed to perform a diagnostic ultrasound scan. A second accessory panel 32 is flexible connected to the bottom edge of the instrument panel 30 such that the second accessory panel 32 may be folded over the instrument panel 30, and the first accessory panel 28 and lay substantially parallel to both panels 28, 30. The second accessory panel 32 has a substantially form fitted pocket 24' for retention of a container of acoustic gel 62, and one or more pockets 24 for the secure retention of accessory products needed to perform a diagnostic ultrasound scan, such that the carrying case 10 arranges the lightweight ultrasound device 20, the data recording device 22 and all accessories at the ready when opened, and securely positioned when closed. In this manner the carrying case 10 may be opened and closed easily and quickly.

In operation, it is preferable that the pockets 24 of the carrying case 10 are not over loaded so as to prevent the proper closing of the carrying case 10 for transport. Furthermore, the arrangement of having the instrument panel 30 centered in the carrying case 10 (between accessory panels 28, 32) is so when the case is laid on a surface, the accessory panels 28, 32 are lifted and turned (like opening a book) so as not to move the delicate instruments. However there is no requirement that the instrument panel 30 be between the two accessory panels 28, 32. It could well be there are some uses where the instrument panel is preferably one of the outer panels. Such might be the case where the carrying case 10 is frequently used in a vertically hanging position using a hanger hook 38. In this configuration it may be preferred to have the instrument panel 30 on the bottom so as to not create a "wrinkle" in the hanging of the carrying case 10.

The panels of the carrying case 10, can be substantially inflexible, or can be extremely flexible, as when the body of the carrying case is made of fabric. In either situation, the carrying case is preferably made from a fabric like material that is sewn together, the carrying case 10 being formed from an outer layer or shell 12, and an inner layer or lining 14 can then be sewn into partitions creating the instrument panel 30, and the accessory panels 28, 32. The outer layer may have material that presents a rubber-like or textured surface to resist sliding when the carrying case is in use. Preferably, the carrying case is made from fabric sewn together, and any inflexibility is imparted to the panels or leaves through the insertion of some sort of board (not shown) between the shell 12 and the lining 14. In this manner the stiffness of the panels may be made as desired, and can even be changed after production if needed. Not only can the stiffness be easily modified, but padded inserts can also be placed into the panels. In the preferred embodiment the carrying case 10 has an instrument panel (the center panel, or second leaf) that has a reinforced structure (is relatively inflexible) and two softer accessory panels (the first and third leaves) which do not have inflexible inserts.

Pockets 24 are sewn into the lining 14 at desired places of the accessory panels 28, 32. A pocket 24 may also be sewn into the instrument panel 30 for the storage of peripherals (i.e. transducers 48, ECG module 50 or other probes 52) for use with the lightweight ultrasound device 20. The pockets may be closable, as with the use of a zipper, a flap that fastens to the pocket (using a snap clasp, Velcro or other common fastener). The pockets 24 may also be made of a fabric that permits a person to see the contents of the pocket without opening it. The fabric may be clear, or have openings (mesh style) to facilitate viewing.

In use, the carrying case 10 is designed primarily to be laid open on a nearly horizontal surface. The carrying case can be laid open on a tray, table or even a bed the patient to be scanned in laying on. Because the carrying case is designed for use with a lightweight ultrasound device, the weight of the carrying case and bag should not be a burden to a patient even if part of the carrying case is laid open on the patient's body. Alternatively, the present invention provides for the carrying case to be hung vertically, using a hanger like device 38 so the carrying case can be hung in the open configuration from a shelf, IV pole or the like. In this manner the horizontal footprint of the carrying case is minimized, yet a physician still has full access to all the instruments and accessories within the carrying case needed to perform an ultrasound diagnostic exam.

When the physician is transporting the lightweight ultrasound device, the case folds up into a slim briefcase, though dimensions may be somewhat taller and longer than the average briefcase. A handle is provided on the top of the carrying case. The handle is attached to a spine inserted into the top margin 40. Alternatively or in addition, a shoulder strap 36 can be used to facilitate transport of the carrying case 10. The spine 16 preferably extends the length of the top margin, and is sewn between the shell 12 and lining 14 such that it cannot migrate. The bottom margin is preferably padded to reduce impact shock to the contents of the carrying case when it is set on the ground. The carrying case 10 may be designed to stand vertically when set down through the use of inflexible inserts in the panels (leaves) and providing for a minimum angle (about 90 degrees) limit to the amount of movement the bottom margin 42 experiences relative to the bottom panel (third leaf) and the instrument panel (second leaf). The carrying case 10 also has one or more fasteners 26 use to keep the carrying case closed during transport. The fasteners may be any type commercially available. In the preferred embodiment, the fasteners are buckle clips (similar to those used for back packs) and Velcro strips along the lining 14 and shell 12 where the accessory panels (first and third leaves) overlap.

There has been described a carrying case for use with a lightweight ultrasound device and an array of accessory products to facilitate transport of the equipment and allow rapid set up and take down to perform and record a diagnostic examination. While the invention has been described with reference to specific embodiments, the description is illustrative of the invention and is not to be construed in a limiting the invention. For example, while the pocket arrangements are shown with transducers and other probes near the ultrasound device, customized pockets can be made on any available surface to house them. In addition, the material need not be sewn together, in a production model the shell and lining could be prefabricated together, and panel elements joined by hinges. Thus, various modifications and applications may occur to those skilled in the art without departing from the true spirit and scope of the invention as defined by the appended claims.

What is claimed is:

1. A carrying case dimensioned to present a lightweight ultrasound device and one or more accessory products in an organized fashion, to a physician to reduce set up time for diagnostic examinations, the carrying case having a handle and at least one fastener for securing the carrying case in a closed configuration, the carry case comprising;

at least one instrument panel, said instrument panel having a top edge and a bottom edge, and having a plurality of harnesses for the secure positioning of a lightweight ultrasound device, a data recording device and at least one transducer, the instrument panel being substantially inflexible;

a first accessory panel being flexibly connected to the top edge of said instrument panel such that the first accessory panel may be folded over said instrument panel such that said first accessory panel and said instrument panel lay substantially parallel, said first accessory panel having one or more pockets for the secure retention of accessory products needed to perform a diagnostic ultrasound scan; and a second accessory panel being flexible connected to the bottom edge of said instrument panel such that the second accessory panel may be folded to lay substantially parallel to said instrument panel, and said first accessory panel, and having a substantially form fitted pocket for retention of a container of acoustic gel, and one or more pockets for the secure retention of accessory products needed to perform a diagnostic ultrasound scan, such that the carrying case arranges the lightweight ultrasound device, the data recording device and all accessories at the ready when opened, and securely positioned when closed, such that the carrying case may be opened and closed easily and quickly.

2. The carrying case as described in claim 1, wherein the instrument panel further comprises one or more pockets on an interior surface.

3. The carrying case as described in claim 1, wherein one or more of the pockets are closable.

4. The carrying case as described in claim 1, wherein the pockets further comprise a material permitting the contents of the pockets to be viewed without opening said pocket(s).

5. The carrying case as described in claim 1, further comprising a shoulder strap.

6. The carrying case a as described in claim 1, wherein one or more of the panels are padded.

7. The carrying case as described in claim 1, wherein two or more of the panels have an inflexible insert.

8. The carrying case as described in claim 1, wherein the plurality of harnesses for the lightweight ultrasound device, data recording device and said transducer are arranged to permit the use of the lightweight ultrasound device, data recording device and said transducer without removing said lightweight ultrasound device or said data recording device from the harnesses, and permit a user full access to a control interface on said lightweight ultrasound device, said data recording device, or said transducer.

9. The carrying case as described in claim 1, wherein the data recording device is a printer, personal digital assistant (PDA), telemetry device or other device to transmit or document an ultrasound examination.

10. The carrying case as described in claim 1, wherein the data recording device is any suitable peripheral device for use with a lightweight ultrasound device.

11. The carrying case as described in claim 1, further comprising one or more pockets on an exterior surface.

12. The carrying case as described in claim 1, further comprising a second fastener for maintaining the carrying case in a closed configuration.

13. The carrying case as described in claim 1, further comprising a hanger hook such that the carrying case may be hung vertically in the open position.

14. The carrying case as described in claim 1, being stain resistant or water resistant.

15. The carrying case as described in claim 1, wherein said at least one transducer further comprises transducers, one or more ECG modules or one or more probes.

16. A carrying case for holding a lightweight ultrasound device, formed in a tri-fold arrangement such that the carrying case may be easily transported when closed, and permit easy access to the hand held ultrasound device when open, the tri-fold arrangement comprising:
  a top panel having an interior face having a flat panel display and a harness for securing said flat panel display in place, an exterior face, and a first fastening element;
  a top margin having a support spine for the attachment of at least one weight bearing handle, the top margin being connected to the top panel;
  a reinforced center panel connected to the top margin, opposite the top panel, the center panel having a harness for firmly holding a lightweight ultrasound device, and a means for attaching a data storage device and a means for attaching a power supply for said flat panel display;
  a padded bottom margin connected to the center panel; and
  a bottom panel being connected to said bottom margin opposite the center panel, the bottom panel having an interior surface having one or more pockets and an exterior surface having a second fastening element wherein when the top panel and bottom panel are folded over the center panel, the top margin and bottom margin form perpendicular support structures, and the first fastening element and the second fastening element may be connected to secure the top panel and the bottom panel in a closed position.

17. The carrying case as described in claim 16, further comprising a padded insert placed between the lightweight ultrasound device, and the flat panel display when in the closed position.

18. The carrying case as described in claim 16, wherein the center panel further comprises one or more pockets.

19. The carrying case as described in claim 16, wherein one or more of the pockets are closable.

20. The carrying case as described in claim 16, wherein the pockets further comprise a material permitting the contents of the pockets to be viewed without opening the pocket.

21. The carrying case as described in claim 16, further comprising a shoulder strap.

22. The carrying case as described in claim 16, wherein one or more of the panels are padded.

23. The carrying case as described in claim 16, wherein two or more of the panels have an inflexible insert.

24. The carrying case as described in claim 16, wherein the harness for the lightweight ultrasound device, and the means for attaching the data storage device are arranged to permit the use of the lightweight ultrasound device and the data storage device without removing said lightweight ultrasound device or the data storage device from the center panel.

25. The carrying case as described in claim 16, wherein the means for attaching the data storage device is a harness.

26. The carrying case as described in claim 16, wherein the data storage device is a printer, personal digital assistant (PDA), telemetry device or other device to transmit or document an ultrasound examination.

27. The carrying case as described in claim 16, wherein the data storage device is any suitable peripheral device for use with a lightweight ultrasound device.

28. The carrying case as described in claim 16, wherein the exterior surface of the panels may have one or more pockets.

29. The carrying case as described in claim 16, further comprising a hanger hook such that the carrying case may be hung vertically in the open position.

30. The carrying case as described in claim 16, being stain resistant or water resistant.

31. The carrying case as described in claim 16, wherein the case may stand vertically.

32. A carrying case for a hand held ultrasound device comprising:
  a flexible tri-leaf body formed from an outer shell and an inner lining sewn together, wherein a margin separates each leaf, the body forming a carrying case when properly folded, and lies substantially flat when open, the tri-leaf body comprising;
  a first leaf;
  a second leaf having a substantially rigid insert between said shell and said lining, the second leaf having a harness for securely retaining a hand held ultrasound device, a mounting area for one or more peripheral device(s);
  a third leaf;
  a first margin separating said first leaf and said second leaf, wherein a weight bearing spine is constructed between said shell and said lining so that a handle may be attached to the spine and support the weight of the carrying case when closed;
  a second margin separating said second leaf and said third leaf, wherein a protective padding is inserted between said shell and said lining; and
  a reusable fastening means for securing the carrying case in the closed position.

33. The carrying case as described in claim 32, further comprises one or more pockets.

34. The carrying case as described in claim 33, wherein said one or more of the pockets are closable.

35. The carrying case as described in claim 33, wherein said one or more pockets further comprise a material permitting the contents of said pockets to be viewed without opening said pockets.

36. The carrying case as described in claim 32, further comprising a shoulder strap.

37. The carrying case as described in claim 32, wherein one or more of the leaves are padded.

38. The carrying case as described in claim 32, wherein two or more of the leaves have an inflexible insert.

39. The carrying case as described in claim 32, wherein the harness for the hand held ultrasound device, and the mounting area for said one or more peripheral devices are arranged to permit the use of the hand held ultrasound device, and one or more peripheral devices without removing said hand held ultrasound device from said harness and permit a user full access to a control interface on said hand held ultrasound device, and access to said one or more peripheral devices.

40. The carrying case as described in claim 32, wherein the one or more peripheral devices can be a data storage device, a printer, personal digital assistant (PDA), telemetry device or other device to transmit or document an ultrasound examination.

41. The carrying case as described in claim 40, wherein the data storage device is any suitable peripheral device for use with a hand held ultrasound device.

42. The carrying case as described in claim 32, further comprising a second reusable fastening means for maintaining the carrying case in a closed configuration.

43. The carrying case as described in claim 32, further comprising a hanger hook such that the carrying case may be hung vertically in the open position.

44. The carrying case as described in claim 32, being stain resistant or water resistant.

45. The carrying case as described in claim 32, wherein the peripheral devices are one or more transducers, ECG modules or probes.

46. The carrying case as described in claim 32, wherein the case may stand vertically.

* * * * *